(12) United States Patent
Behrends et al.

(10) Patent No.: US 9,675,701 B2
(45) Date of Patent: Jun. 13, 2017

(54) COLOURED DISINFECTANT PREPARATION BASED ON BISPYRIDINIUMALKANE

(71) Applicant: L'AIR LIQUIDE, SOCIETE ANONYME POUR L'ETUDE ET L'EXPLOITATION DES PROCEDES GEORGE, Paris (FR)

(72) Inventors: Sabine Behrends, Appen (DE); Andreas Dettmann, Hamburg (DE); Mona Hahn, Luneburg (DE); Nadine Radischat, Hamburg (DE); Carsten Vollmann, Hamburg (DE)

(73) Assignee: L'AIR LIQUIDE, SOCIETE ANONYME POUR L'ETUDE ET L'EXPLOITATION DES PRECEDES GEORGES CLAUDE, Paris (FR)

( * ) Notice: Subject to any disclaimer, the term of this patent is extended or adjusted under 35 U.S.C. 154(b) by 106 days.

(21) Appl. No.: 14/718,911

(22) Filed: May 21, 2015

(65) Prior Publication Data
US 2015/0335757 A1 Nov. 26, 2015

(30) Foreign Application Priority Data
May 26, 2014 (DE) .......... 10 2014 107 412

(51) Int. Cl.
*A61K 47/46* (2006.01)
*A61L 9/00* (2006.01)
(Continued)

(52) U.S. Cl.
CPC .............. *A61K 47/46* (2013.01); *A01N 43/40* (2013.01); *A61K 31/444* (2013.01);
(Continued)

(58) Field of Classification Search
CPC .. A61K 47/46; A61K 31/4425; A61K 31/444; A61K 47/22; A61K 47/20; A61L 9/00; A61L 2/00; A61L 2/18; A01N 43/40
See application file for complete search history.

(56) References Cited

U.S. PATENT DOCUMENTS 5,032,382 A 7/1991 Grollier et al.
5,053,240 A 10/1991 Todd, Jr.
(Continued)

FOREIGN PATENT DOCUMENTS

DE 38 31 920 A1 4/1989
DE 40 33 690 A1 4/1991
(Continued)

OTHER PUBLICATIONS

Rompp Lexikon Chemie, Stichworte: "Xanthenfarbstoffe", "Erythrosin", "Eosin", "Phioxin", "Rhodamine", "Echtgelb"; 13-Carotin, "Bixin", "Norbixin", Luteini Version 4.0. [URL: https:llroempp.thieme.de/roempp4.0/do/Welcome.do]. [recherchiert am Feb. 25, 2015]. gutachtlich.
(Continued)

*Primary Examiner* — Trevor Love
(74) *Attorney, Agent, or Firm* — Young & Thompson

(57) ABSTRACT

The non-solid disinfectant preparation includes a) bispyridiniumalkane (in particular octenidine) and b) dye selected from xanthene dyes, azo dyes and polyterpene compounds. The preparation is free from fluorescein and salts thereof. The novel preparations exhibit an excellent remanence effect.

17 Claims, 1 Drawing Sheet

(51) Int. Cl.
  *A61L 2/00* (2006.01)
  *A01N 43/40* (2006.01)
  *A61K 31/4425* (2006.01)
  *A61L 2/18* (2006.01)
  *A61K 31/444* (2006.01)
  *A61K 47/22* (2006.01)
  *A61K 47/20* (2006.01)

(52) U.S. Cl.
  CPC .......... *A61K 31/4425* (2013.01); *A61K 47/20* (2013.01); *A61K 47/22* (2013.01); *A61L 2/00* (2013.01); *A61L 2/18* (2013.01); *A61L 9/00* (2013.01)

(56) References Cited

U.S. PATENT DOCUMENTS

| | | |
|---|---|---|
| 5,244,666 A | 9/1993 | Murley |
| 5,354,906 A | 10/1994 | Weitemeyer et al. |
| 2001/0036963 A1 | 11/2001 | Behrends et al. |
| 2008/0020006 A1 | 1/2008 | Andre |
| 2008/0108674 A1 | 5/2008 | Magallon et al. |
| 2011/0177202 A1 | 7/2011 | Christiansen et al. |
| 2013/0142909 A1 | 6/2013 | Klingenberg |
| 2014/0081221 A1 | 3/2014 | McDonald et al. |
| 2014/0081222 A1 | 3/2014 | McDonald et al. |

FOREIGN PATENT DOCUMENTS

| | | |
|---|---|---|
| DE | 41 37 548 A1 | 5/1993 |
| DE | 196 47 692 A1 | 6/1998 |
| DE | 199 01 526 A1 | 7/2000 |
| DE | 10 2005 045 145 A1 | 3/2007 |
| DE | 10 2007 030 416 A1 | 1/2009 |
| DE | 10 2011 056 111 A1 | 6/2013 |
| DE | 10 2012 215 511 A1 | 6/2014 |
| EP | 560 114 A | 9/1993 |
| EP | 2 345 336 A1 | 7/2011 |
| WO | 97/46622 A1 | 12/1997 |
| WO | 00/63337 A | 10/2000 |
| WO | 02/082907 A1 | 10/2002 |
| WO | 02/091832 A1 | 11/2002 |
| WO | 03/015531 A2 | 2/2003 |
| WO | 2004/083905 A2 | 9/2004 |
| WO | 2005/123013 A1 | 12/2005 |
| WO | 2006/028025 A1 | 3/2006 |
| WO | 2006/077616 A1 | 7/2006 |
| WO | 2007/062306 A2 | 5/2007 |
| WO | 2007/100654 A2 | 9/2007 |
| WO | 2007/130981 A2 | 11/2007 |
| WO | 2008/032212 A2 | 3/2008 |
| WO | 2009/058144 A1 | 5/2009 |
| WO | 2009/138890 A2 | 11/2009 |
| WO | 2011/006263 A1 | 1/2011 |
| WO | 2014/043199 A1 | 3/2014 |
| WO | 2014/043354 A1 | 3/2014 |
| WO | 2014/151331 A1 | 9/2014 |

OTHER PUBLICATIONS

DE Office Action, dated Apr. 1, 2015, from corresponding DE application.

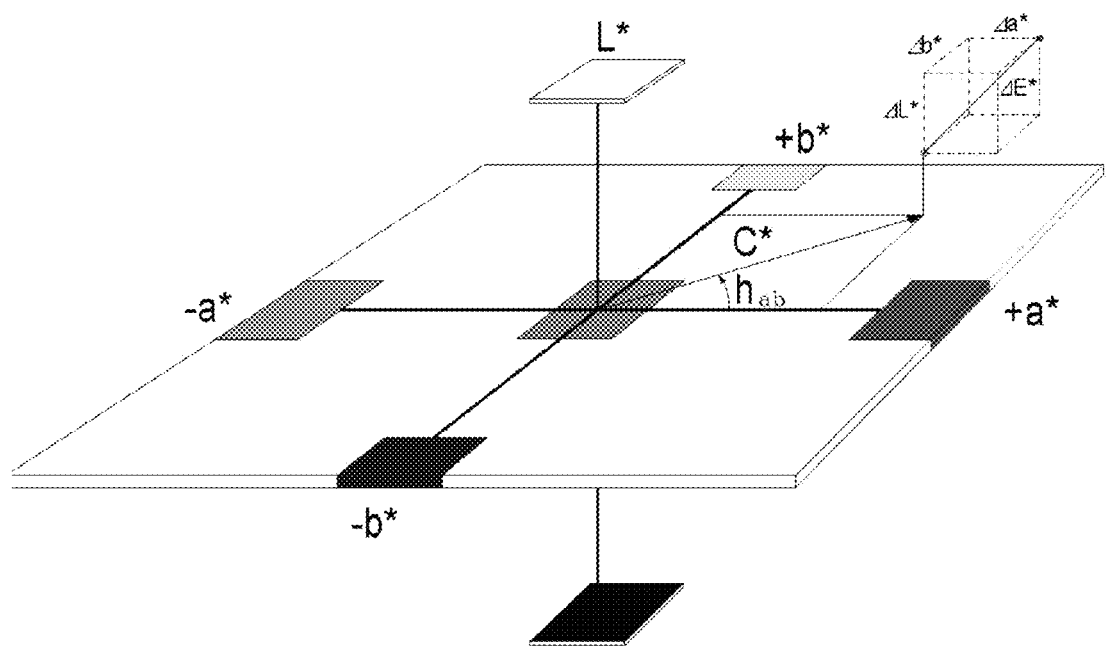

COLOURED DISINFECTANT PREPARATION BASED ON BISPYRIDINIUMALKANE

FIELD OF THE INVENTION

The present invention relates to a non-solid disinfectant preparation which comprises a) bispyridiniumalkane and b) specific dye. In addition, the invention relates to this preparation for use in a method for the disinfection of skin, mucosa or wounds. Moreover, the invention relates to the use of the dyes for colouring a non-solid disinfectant preparation which comprises bispyridiniumalkane.

BACKGROUND OF THE INVENTION

For certain applications of antiseptic disinfectants, a coloured marking of the treated surface (such as skin or mucosa) is desired, for example before a surgical intervention or during an operation.

Besides compositions based on the active ingredient PVP-iodine, which are already coloured brown-red on account of the coloration of the active ingredient, there are coloured skin antiseptics on the market, where the active ingredients are for example nonionic (e.g. Kodan® tincture forte coloured, with 45% by weight of 2-propanol, 10% by weight of 1-propanol, 0.2% by weight of 2-biphenylol, $H_2O_2$, E104, E110, E151). The group of cationic antiseptic active ingredients for skin antiseptics includes chlorhexidine digluconate (hereinbelow "chlorhexidine"), which has been successful on the US market in formulations with 70% 2-propanol (e.g. the product Chloraprep® from Carefusion, formerly Enturia). In principle, however, there are concerns regarding chlorhexidine-containing antiseptics, specifically on account of the possible formation of p-chloroaniline (carcinogenic, toxic) as one possible degradation product upon storage. Moreover, on account of the comparatively low efficacy of chlorhexidine, higher active ingredient concentrations are required in the product. On account of the high active ingredient concentrations in these products, for antiseptics based on chlorhexidine, any loss in efficacy upon adding small amounts of dyes is not a problem.

DE 41 37 548 A1 discloses antimicrobial active ingredient combinations based on acridine dyes (which have their own antimicrobial effect), optionally in combination with further antimicrobial active ingredients. Carcinogenic properties are discussed for acridine dyes; use in disinfectant preparations for application to the human skin is accordingly not possible.

DE 199 01 526 A1 discloses an antiseptic which comprises defined amounts of 1-propanol, 2-propanol and ethanol. Furthermore, the optional presence of dyes is provided. Problems due to the interaction of antiseptic active ingredients with specific dyes is not discussed in DE 199 01 526 A1.

DE 10 2007 030 416 A1 describes alcoholic antiseptics which comprise 50 or more % by weight of alcohol having 1 to 3 carbon atoms, dye and optionally further antimicrobial active ingredients. Besides a broad multitude of dyes, a broad multitude of optional antimicrobial additives is disclosed. However, compositions which obligatorily comprise 50 or more % by weight of alcohol are undesired.

WO2007/062306 A2 describes processes for coating surfaces. In this process, a composition which comprises antimicrobial agent is cured on the surface by means of heat, where the composition can comprise a dye. Typically, the surface is an inanimate surface (for example a medical device). The use of compositions for the antiseptic treatment of animate surfaces is not described.

WO2007/130981 A2 describes aqueous solutions of chlorhexidine and a cationic dye. However, chlorhexidine in antiseptics for use in the oral cavity turns the teeth and the tongue brownish. Also, after prolonged use, the sense of taste can be adversely affected. EP 2 499 913 A1 also deals with chlorhexidine-containing antiseptic solutions, and anionic dyes are proposed for their colouring.

WO97/46622 A1 describes the use of natural or nature-identical synthetic dyes for the marking or inking of materials. By way of example, mention is made of the temporary marking of operation areas using dye-containing desinfection solution or coloured pens on the skin. The fact that certain active ingredients of disinfectants have a remanence effect which must not be influenced by the dye used is not discussed in WO97/46622 A1.

WO03/015531 A2 describes a pharmaceutical formulation which comprises a dye and has a content of opiate.

DE 40 33 690 A1 discloses adducts of norbixin with water-soluble or water-dispersible proteins or branched-chain or cyclic polysaccharides. Norbixin is a carotenoid with two carboxylic acid groups obtained from annatto seeds. Bixin is the monomethyl ester of norbixin. The adducts are used for example for colouring milk. The colouring of surfaces by means of coloured disinfectants is not discussed.

WO2005/123013 A1 discloses the use of amino-substituted hydroxybenzophenone compounds for stabilizing the colour of cosmetic and dermatological preparations.

WO02/091832 A1 describes two-component disinfection systems, where the first component comprises chlorite and the second component comprises acid and optionally oxidizable dye. By adding α-olefinsulfonate, the generation of chlorine dioxide upon combining the two components is reduced, as a result of which the dye present is oxidatively attacked to a lesser extent and is available for marking disinfected areas. According to the teaching of WO02/091832 it is also not important that the remanence effect of an active ingredient is not adversely affected by an added dye. Moreover, the use of two-component disinfectants is complex and consequently not suitable for use in the hospital sector.

WO2006/028025 A1 describes antibacterial compositions with a content of special benzopyranones.

WO2006/077616 A1 deals with a system for the visualization of contaminated areas using a film with controlled release of coloured substances.

WO2007/100654 A2 discloses a method for controlling microorganisms in which a surface is coated with a removable composition forming an antimicrobial film.

WO2008/032212 A2 relates to coloured or colourable foamable compositions for topical applications where the coloration of the composition differs from that of the foam produced therefrom.

According to DE 38 31 920 A1, a photostable cosmetic composition for protecting the human epidermis against UV radiation is said to comprise a combination of bixin with fat-soluble UV-ray-absorbing compound.

WO2009/138890 A2 describes a wipe made of fibre material, where beads are included in the fibre material and the beads include an active ingredient. Upon wetting the beads, they break open and release the active ingredient.

WO2011/006263 A1 relates to coloured antibacterial compositions for mouth disinfection. The compositions can comprise dye.

EP 2 345 336 A1 teaches a dye composition which comprises a mixture of two special emulsifiers.

DE 10 2011 056 111 A1 relates to an emulsion with an aqueous phase and oil phase dispersed therein, with a dye being present in the oil phase. The dye is preferably a carotenoid, and the emulsifier in the aqueous phase is a saponin, which is used in combination with esters from plant lipid and food acid for emulsification.

U.S. Pat. No. 5,244,666 A describes surgical and wound disinfectants with a content of quaternary ammonium compound and dye.

WO02/082907 A1 describes complexes of antiseptics with dyes. By way of example, compositions with chlorhexidine are described which, as mentioned above, is undesired.

WO2004/083905 A2 describes an applicator for applying a liquid which is coloured in the applicator. For this purpose, in the applicator there is a glass ampoule filled with the liquid, and upon breaking open the ampoule the liquid flows through a porous element (such as a felt) which comprises dye. The dyed composition is then applied to the desired surface. A stability of a mixture of antiseptic active ingredient and dye is not an issue here, nor is the fact that the antiseptic active ingredient has to remain antimicrobially effective even upon prolonged contact with the dye.

According to WO2014/043354 A1 (US2014/0081222 A1), an antiseptic based on chlorhexidine or octenidine is applied with the help of a hydrophilic, solid (polyurethane) foam. According to WO2014/043199 A1 (US2014/0081221 A1), the solid (polyurethane) foam is hydrophobic. The antiseptic can be coloured or be coloured by dye present in the foam.

WO2009/058144 A1 discloses an antiseptic solution which comprises a micellar complex and a cationic antiseptic active ingredient, where the micellar complex consists of cationic auxiliary and anionic dye. Examples of cationic auxiliaries are quaternary ammonium compounds.

According to the teaching of WO2009/058144 A1, the cationic auxiliary is supposed to prevent an insoluble precipitate forming from the anionic dye and the cationic antiseptic active ingredient. In an alternative, a separate catonic auxiliary is added which forms the micellar complex with the anionic dye. Alternatively, it is possible to use a superstoichiometric amount of cationic antiseptic active ingredient (superstoichiometric with regard to the molar amount of anionic dye). Moreover, it was tested over a period of 24 hours whether precipitates result.

A stipulated comparatively large amount of cationic agent (namely cationic auxiliary and additionally cationic antiseptic agent, or alternatively a large amount of antiseptic active ingredient), however, is undesired. Moreover, testing over just 24 hours is not very meaningful. Since an applicator is used for applying the solution in which the disinfectant comes into contact with the dye dissolved out of a felt only for a comparatively short period, a stability of dye in contact with the antiseptic active ingredient over a prolonged period and a high remanence effect of the antiseptic active ingredient are not decisive according to the teaching of WO2009/058144 A1.

The medicament and surgical skin antiseptic Octeniderm® has hitherto been approved as a colourless product. It comprises 0.1% by weight of octenidine dihydrochloride ("octenidine" for short hereinbelow) as remanent active ingredient (and 30% by weight of 1-propanol, 45% by weight of 2-propanol, remainder: completely demineralized water). Octenidine is a quaternary ammonium compound of the imine type (cation) with chloride as anion and can be inhibited by the vast majority of anionic dyes in its antiseptic efficacy. Since Octeniderm® comprises only 0.1% octenidine, dyes added for colouring the skin in a relatively high concentration (up to 0.5% as in the case of products containing chlorhexidine) can lead to a long-term (up to 24 hours) significant reduction in the remanent effect of octenidine.

It has been found that the triphenylmethane dye Patent Blue V, despite its anionic character, shows no restriction of the efficacy of the octenidine in Octeniderm®. However, blue dyes are not accepted by the market on account of the poor visibility of the vessels under the skin.

SUMMARY OF THE INVENTION

It was therefore an object of the present invention to provide a coloured non-solid preparation in which the efficacy of bispyridiniumalkanes (such as octenidine) is not inhibited and which can be approved even with the added dye. Furthermore, it was an object of the present invention to provide those preparations which can be stored over a prolonged period and in so doing do not tend towards precipitates that are disadvantageous for metered addition, and specifically without additional auxiliaries having to be added which prevent merely the formation of precipitates or the inhibition of the antiseptic effect and which contribute nothing to the antiseptic effect. Moreover, the preparations should not have to comprise 50 or more % by weight of alcohol having 1 to 3 carbon atoms. Moreover, the preparations should also be stable and effective over a period of 24 hours.

The search for suitable dyes has been hindered by the fact that hitherto there was no method available with which the in vitro efficacy of remanent active ingredients could be tested in the case of the simultaneous presence of large amounts of immediately acting agents, such as alcohols (the prior art is a skin experiment with resident flora). For example, in preliminary experiments relating to the present invention carried out with a new type of method, it has been found that in preparations which comprise fluorescein or its disodium salt (uranine), the remanence effect of octenidine is inhibited.

It has now been found that this object is achieved by a non-solid disinfectant preparation which comprises
  a) one or more bispyridiniumalkanes and
  b) one or more dyes selected from xanthene dyes, azo dyes and polyterpene compounds,
where the preparation is free from fluorescein and its salts.

BRIEF DESCRIPTION OF THE DRAWINGS

FIG. 1 illustrates a three-dimensional CIE-L*a*b* model.

DETAILED DESCRIPTION OF THE INVENTION

The invention is based inter alia on the fact that the specified dyes, although they have an anionic part structure, do not inhibit the long-term effect of bispyridiniumalkane.

1. Bispyridiniumalkane

The term bispyridiniumalkane here includes the bis[4-(substituted amino)-1-pyridinium]alkanes disclosed in DE 27 08 331 C2 and of the general formulae (I) or (II)

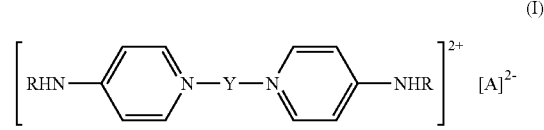

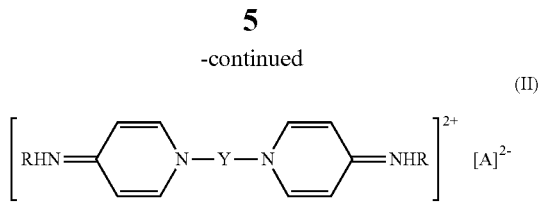

(II)

in which
- Y is an alkylene group having 4 to 18 carbon atoms,
- R is an alkyl group having 6 to 18 carbon atoms or a cycloalkyl group having 5 to 7 carbon atoms or the phenyl radical, which is substituted by a halogen atom, and
- A is one or more anions.

The aforementioned definition of A is strictly speaking valid for mono- and divalent anions, although A can of course also be a polyvalent anion, e.g. phosphate or orthosilicate. Furthermore, the term bispyridiniumalkane includes the various prototropes of the compounds of the formula (I), as is disclosed for example in DE 196 47 692 A1.

In all embodiments of the invention, however, it is preferred that the bispyridiniumalkane is octenidine dihydrochloride (R=n-octyl, Y=n-decenyl; A=2×Cl, "octenidine"). Component a) is thus particularly preferably octenidine.

Preferred amounts of component a) in the preparation according to the invention are 0.005 to 1.0% by weight, preferably 0.01 to 0.5% by weight, more preferably 0.03 to 0.3% by weight, even more preferably 0.04 to 0.2% by weight, such as 0.05 to 0.15% by weight, for example about 0.1% by weight, in each case based on the total weight of the preparation.

2. Dyes

The preparation comprises, as component b), one or more dyes selected from xanthene dyes, azo dyes and polyterpene compounds. However, neither fluorescein nor its salts (such as the disodium salt, uranine) are present in preparations according to the invention.

The amount of component b) is typically 0.01 to 0.2% by weight, preferably 0.02 to 0.1% by weight.

i. Xanthene Dyes

Xanthene is a tricyclic ether. The xanthene dyes, for example the rhodamines, as well as eosin B and eosin Y, have the basic structure of xanthene:

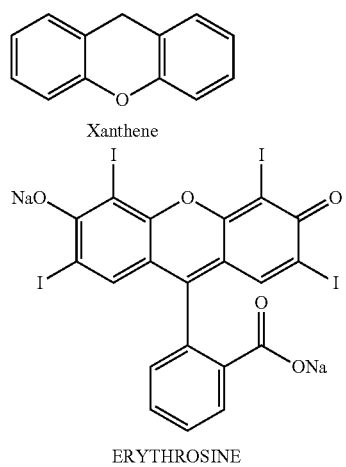

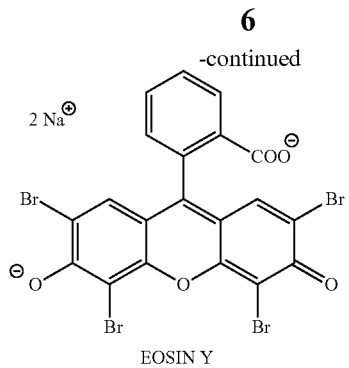

EOSIN Y

D&C RED 27 is 2',4',5',7'-tetrabromo-4,5,6,7-tetrachloro-fluorescein (2',4',5',7'-tetrabromo-4,5,6,7-tetrachloro-3',6'-dihydroxyspiro[isobenzofuran-1(3H),9'-[9H]xanthen]-3-one).

Preferably, the xanthene dye is not D&C Orange 5. Particularly preferably, D&C Orange 5 is not present in the preparation.

It is also preferred that the preparation according to the invention comprises no kind of fluorescein or fluorescein derivatives, such as, for example, fluorescein salts or halogen-substituted derivatives or salts thereof.

The xanthene dye is preferably selected from erythrosine, eosin, D&C Red 27 and phloxine B, where component b) is particularly preferably erythrosine.

ii. Azo Dyes

The azo dye is preferably a monoazo dye, where the monoazo dye is preferably selected from D&C Orange 4, fast yellow and D&C Red 33, where component b) is in particular D&C Orange 4.

iii. Polyterpene Compounds

The polyterpene compound is preferably an isoprenoid, in particular a carotenoid, where the carotenoid is in turn preferably selected from carotene dyes and xanthophyll dyes.

Carotenes are pure hydrocarbons, xanthophylls are oxygen-oxidized hydrocarbons. Frequently occurring primary carotenoids are β-carotene, a representative of the carotenes, as well as lutein, violaxanthin and neoxanthin as representatives of the xanthophylls.

The xanthophyll dye is for example selected from lutein and the annatto dyes cis- or trans-bixin and cis- or trans-norbixin, where component b) is in particular lutein (4-[18-(4-hydroxy-2,6,6-trimethylcyclohex-2-enyl)-3,7,12,16-tetra-methyloctadeca-1,3,5,7,9,11,13,15,17-nonaenyl]-3,5,5-trimethylcyclohex-3-enol, E161b).

If the dye is E160b (annatto, bixin, norbixin), then it is preferably stabilized (for example with propylene glycol and polysorbate 80, commercial product Annatto® 2% AS).

Norbixin (a xanthophyll) is a natural dye which is obtained by extraction from the seeds of the urucum or achiote plant annatto (*Bixa orellana*). Norbixin can be obtained by removing the outer layer of the prepared seeds of the annatto bush (*Bixa orellana*) by rubbing off the seeds in cold water and subsequent extraction by solvents such as, for example, acetone, methanol or hexane. The solution resulting therefrom is acidified bixin (and specifically the methyl ester of the acid norbixin), which is then filtered and dried, and the precipitate is ground. The precipitate comprises primarily cis- and trans-bixin, where the main dye is the cis-bixin. With alkaline hydroxide solution, norbixin can be obtained as the corresponding salt, where likewise again cis-norbixin is the main dye.

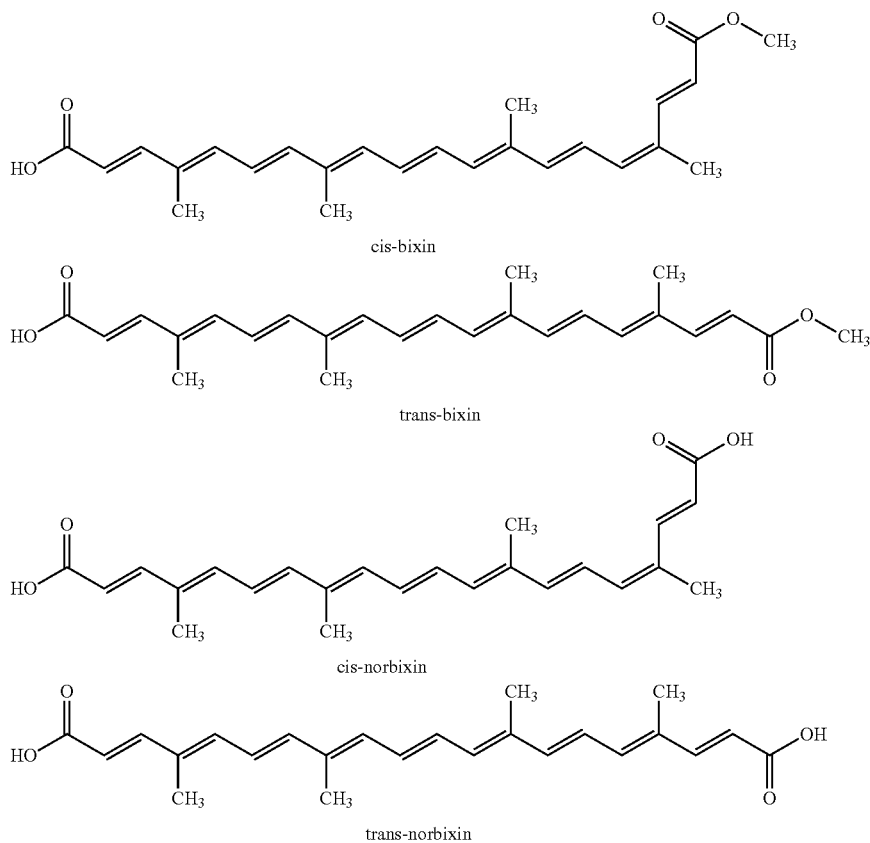

The carotene dye is for example selected from beta-carotene and 8'-apo-beta-caroten-8'-al.

8'-Apo-β-caroten-8'-al is a carotenoid. It occurs naturally e.g. in oranges, vegetables and liver, but is nowadays mainly produced synthetically. In the EU, it is approved as a food additive with the number E 160e.

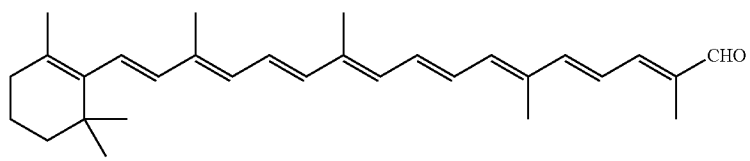

Preferably, component b) consists of erythrosine, eosin, D&C Orange 4 and annatto, and mixtures thereof. Component b) particularly preferably consists of annatto.

3. Optional Constituents

Besides the obligatorily stipulated components a) and b), the preparation according to the invention preferably comprises further constituents, e.g. c) one or more alcohols selected from aliphatic and aromatic alcohols.

Typically and preferably used alcohols are aliphatic alcohols.

The aliphatic alcohol is preferably a $C_2$- to $C_6$-alkyl alcohol, such as, for example, ethanol, propanol, butanol and mixtures thereof, in particular ethanol and propanol and mixtures thereof. The concentration of the aliphatic alcohol in the preparation is typically at least 5% by weight, preferably at least 30% by weight, more preferably at least 40% by weight, in particular 50 to 90% by weight. In the case of n-propanol, low concentrations above 10% by weight are already very effective (in particular between 30 and 50% by weight). In the event of a sole use of an aliphatic alcohol, the use of n-propanol is preferred over the use of isopropanol, and the use of isopropanol over the use of ethanol is preferred. Mixtures of aliphatic alcohols are often present in the preparation.

Ethanol

If ethanol is added as aliphatic alcohol, a preferred amount in the preparation according to the invention is at least 30% by weight, preferably at least 40% by weight, in particular at least 60% by weight, for example at least 80% by weight. If it is specifically a case of controlling aerobic spore-forming bacteria such as *Bacillus* spp., then the amount of ethanol in the preparation is preferably at most 90% by weight, more preferably at most 80% by weight, with an amount of ethanol of 60% by weight being most preferred.

Isopropanol (2-Propanol)

When using isopropanol as aliphatic alcohol, the preferred amount is at least 10% by weight, more preferably at least 30% by weight.

n-Propanol (1-Propanol)

If n-propanol is used as aliphatic alcohol in the preparation, then the concentration is preferably at least 4% by weight, more preferably at least 10% by weight, in particular at least 20% by weight.

Mixtures of Ethanol and Isopropanol

In a further embodiment, the preparation comprises a mixture of ethanol and isopropanol as aliphatic alcohol. Preferred concentrations of ethanol are 60 to 85% by weight, more preferably 65 to 80% by weight, in particular 70 to 80% by weight. Preferred concentrations of isopropanol are 1 to 15% by weight, such as 2 to 12% by weight.

Mixtures of Isopropanol and n-Propanol

In a further preferred embodiment, the preparation comprises a mixture of isopropanol and n-propanol as aliphatic alcohol. The concentration of isopropanol is preferably 5 to 55% by weight, more preferably 15 to 50% by weight, in particular 25 to 50% by weight, such as 28 to 48% by weight. Preferably, the amount of n-propanol is 5 to 50% by weight, preferably 10 to 45% by weight, in particular 20 to 35% by weight.

Mixtures of Ethanol and n-Propanol

In a further preferred embodiment, mixtures of ethanol and n-propanol are used as aliphatic alcohol in the preparation. A preferred concentration of ethanol in the preparation is 10 to 50% by weight, more preferably 20 to 30% by weight, such as for example about 25% by weight. A preferred concentration of n-propanol is 30 to 50% by weight, preferably 35 to 45% by weight.

Mixtures of Ethanol with n-Propanol and Isopropanol

Mixtures of ethanol with isopropanol and n-propanol as aliphatic alcohol are very particularly preferred. A preferred concentration of ethanol is 10 to 30% by weight, such as for example 20% by weight. A preferred amount of isopropanol is 20 to 40% by weight, such as for example 30% by weight. Preferably, the amount of n-propanol is 15 to 35% by weight, such as about 25% by weight.

In all embodiments of the invention, propanol is preferred as aliphatic alcohol, i.e. n-propanol, isopropanol and mixtures thereof.

Alternatively to one or more aliphatic alcohols (or additionally), one or more aromatic alcohols may be present in the preparation according to the invention.

Aromatic Alcohol

The aromatic alcohol (or the optionally two or more aromatic alcohols) is preferably (i) aryloxyalkanol (i.e. glycol monoaryl ether) or (ii) aryl alkanol.

Preferred aryloxyalkanols (i) are selected from phenoxyethanol and phenoxypropanol, preferably phenoxyethanol.

Preferred arylalkanols (ii) are selected from 3-phenyl-1-propanol, phenethyl alcohol, veratryl alcohol, benzyl alcohol or 2-methyl-1-phenyl-2-propanol, preferably 3-phenyl-1-propanol, phenethyl alcohol, veratryl alcohol or 2-methyl-1-phenyl-2-propanol, in particular phenethyl alcohol.

In all embodiments of the invention, it is preferred that the aromatic alcohol is selected from benzyl alcohol, phenoxyethanol and phenethyl alcohol; in particular, phenethyl alcohol or phenoxyethanol are preferred as component b).

In one embodiment of the invention, the aromatic alcohol is not benzyl alcohol because under certain circumstances it can result, depending on the time, in the development of odour as a consequence of the formation of benzaldehyde (because benzyl alcohol is oxidation-sensitive). In one embodiment of the invention, the composition according to the invention is thus free from benzyl alcohol. In an alternative embodiment, if benzyl alcohol is present, one (or more) other aromatic alcohol(s), i.e. different from benzyl alcohol, is (are) moreover also present.

Besides the obligatorily stipulated components a) and b) and the optional presence of c) one or more alcohols (where aliphatic alcohols are preferred as component c), the disinfectant preparation according to the invention comprises, in a preferred embodiment, one or more of the following optional components:

one or more surfactants,
one or more solvents and/or
one or more active ingredients and/or auxiliaries.

Surfactant

As optional constituent, cationic, anionic, amphoteric and/or nonionic surfactants are present in the preparation according to the invention, preferably amphoteric or nonionic surfactants. These surfactants, particularly if they are present in a comparatively small amount, can have an effect supporting the action of the antiseptic active ingredient. If they are present in a relatively high use concentration in the disinfectant, these surfactants can then have an antimicrobial effect or contribute significantly to this effect.

As nonionic surfactant, all suitable nonionic surfactants can be used, where (i) (fatty) alcohol ethoxylates, (ii) sorbitan esters, (iii) alkyl glycosides (in particular alkyl polyglucosides), (iv) amine oxides and (v) ethylene oxide/propylene oxide block copolymers are preferred.

The (i) alcohol polyalkoxylates include fatty alcohol alkoxylates, e.g. isodecyl ethoxylates with different fractions of ethylene oxide, isotridecyl ethoxylates, polyethylene glycol ethers of stearyl, lauryl and cetyl and oleyl alcohol. Here, the alcohols can have been alkoxylated with ethylene oxide, propylene oxide or any desired mixtures of ethylene oxide and propylene oxide. Alcohol polyalkoxylates are known inter alia under the names Lutensol®, Marlipal®, Marlox®, Brij® and Plurafac®. As nonionic surfactant, particular preference is given to lauryl alcohol ethoxylate.

Furthermore, the nonionic surfactants used are (ii) sorbitan esters, which are mostly in the form of oleates, stearates, laurates and palmitates and which are referred to as polysorbates (e.g. Tween®).

Moreover, the nonionic surfactant may be a (iii) alkyl glycoside, such as an alkyl glucoside (i.e. an alkylglycoside of glucose), more preferably a $C_8$- to $C_{20}$-alkylpolyglucose, in particular a $C_8$- to $C_{16}$-alkylpolyglucose of a fatty alcohol, where a laurylpolyglucose, a decylpolyglucose or a mixture thereof is preferred. The carbon chain length in the case of cocoylpolyglucose is 8 to 16 atoms, in the case of laurylpolyglucose is 12 to 16 carbon atoms and in the case of decylpolyglucose is likewise 8 to 16 carbon atoms.

A typical amount of alkyl glycoside is 0.03 to 10% by weight, preferably 0.06 to 5% by weight, in particular 0.1 to 2% by weight.

As (iv) amine oxide, in principle all suitable amine oxides can be used according to the invention. The amine oxides which are N-oxides of tertiary amines include aliphatic amine oxides, cyclic amine oxides (such as N-alkylmorpholine oxide) and aromatic amine oxides (such as pyridine N-oxides). In a preferred embodiment, the amine oxide has the general formula $$R^1R^2R^3N\text{—}O,$$

in which $R^1$ is methyl, ethyl or 2-hydroxyethyl, $R^2$ is methyl, ethyl or 2-hydroxyethyl, $R^1$ and $R^2$ together can be morpholine, $R^3$ is alkyl having 8 to 18 carbon atoms or $R^4$CONH (CH$_2$)$_n$, where R$^4$ is alkyl having 8 to 18 carbon atoms and n is in the range from 1 to 10, preferably 1 to 5, more preferably 2 to 4, and in particular 3, and 2-hydroxyethyl can be condensed with 1 to 2000 ethylene oxide, ethylene oxide/propylene oxide or propylene oxide units.

Examples of amine oxides are cocamidopropylamine oxide, N-cocomorpholine oxide, decyldimethylamine oxide, dimethylcetylamine oxide, dimethylcocamine oxide, dimethyl-hydr. tallow-amine oxide, dimethyllaurylamine oxide, dimethylmyristylamine oxide, (2-hydroxyethyl)cocamine oxide and oleamine oxide. See also "International Cosmetic Ingredient Dictionary and Handbook", 10th edition, 2004, volume 3, pages 2268-2275 (Surfactants-Cleansing Agents).

In a preferred embodiment, the amine oxide is cocamidopropylamine oxide, i.e. R$^4$CO is the acyl radical derived from the fatty acids of coconut oil, n=3, and R1 and R2 are methyl. This product is sold as Rewominox B 204 from Evonik, Federal Republic of Germany.

A typical amount of amine oxide is 0.03 to 10% by weight, preferably 0.06 to 5% by weight, in particular 0.1 to 2% by weight.

Likewise suitable as surfactant are amphoteric surfactants, for example betaines. Suitable betaines are described in EP 560 114 A2. Particular preference is given to cocamidopropylbetaine. A typical amount of betaine is 0.03 to 10% by weight, preferably 0.06 to 5% by weight, in particular 0.1 to 2% by weight.

Moreover suitable as surfactant are cationic surfactants, such as quaternary ammonium salts. In principle, all suitable quaternary ammonium compounds can be used according to the invention. The quaternary ammonium compound is preferably a dialkyldimethylammonium salt.

Quaternary ammonium salts used according to the invention are given by the formula [R$^1$R$^2$R$^3$(CH$_3$)N]$^+$[X]$^-$, where R$^1$ to R$^3$ can be identical or different and are selected from C$_1$- to C$_{30}$-alkyl, aralkyl, -alkenyl and mixed groups, which can have one or more atoms selected from O, S, N and P, where R$^1$ to R$^3$ are for example C$_8$- to C$_{18}$-alkyl, benzyl or methyl, preferably C$_9$- to C$_{18}$-alkyl, benzyl or methyl, such as C$_{16}$-alkyl, benzyl or methyl. X is an anion (an inorganic or organic acid). In this connection, both anion and cation of the quaternary ammonium salt can be polyvalent ions, which gives rise to a stoichiometry [A$^{(n+)}$]$_m$[K$^{(m+)}$]$_n$.

According to the invention, suitable quaternary ammonium salts are all quaternary ammonium salts known in the prior art and of the aforementioned formula, as disclosed for example in WO 00/63337 A, to which reference is made here. However, preference is given to using dialkyldimethylammonium salts, for example dialkyldimethylammonium chlorides, the alkyl chains of which are selected independently of one another from C$_8$- to C$_{18}$-alkyl, preferably C$_9$- to C$_{18}$-alkyl, such as C$_{16}$-alkyl. In the dialkyldimethylammonium salts, one of the methyl groups can be an alkoxylated, for example ethoxylated, hydromethyl group.

Quaternary ammonium salts used with preference according to the invention are compounds of the formulae [R$^1$N(CH$_3$)$_3$]$^+$[X]$^-$, [R$^1$R$^2$N(CH$_3$)$_2$]$^+$[X]$^-$ and [R$^1$R$^2$R$^3$(CH$_3$)N]$^+$[X]$^-$, where R$^1$ to R$^3$, independently of one another, are selected from C$_8$- to C$_{18}$-alkyl and —(CH$_2$—CHR$^4$O)$_n$—R$^5$, where n is a number from 1 to 20, preferably 1 to 5, and R$^4$ and R$^5$, which can be identical or different, are H and/or C$_1$- to C$_4$-alkyl, preferably H.

Examples of anions and classes of anions of the quaternary ammonium salts used according to the invention are hydroxide, sulphate, hydrogensulphate, methosulphate, ethosulphate, lauryl sulphate, lauryl ether sulphate, cellulose sulphate, sulphamate, halide (fluoride, chloride, bromide, iodide), nitrite, nitrate, carbonate, hydrogencarbonate, phosphate, alkyl phosphate, metaphosphate, polyphosphate, thiocyanate (rhodanide), carboxylic acid salt such as benzoate, lactate, acetate, propionate, citrate, succinate, glutarate, adipate, toluenesulphonate (tosylate) and salicylate. Particularly preferred anions are chloride and propionate.

Particular preference is given to using the quaternary ammonium salts mecetronium etilsulphate (hexadecyl(ethyl)dimethylammonium ethyl sulphate) and benzalkonium chloride.

Furthermore, it is preferred that the preparation according to the invention comprises no cetylpyridinium chloride.

In a preferred embodiment, besides the obligatorily present component a) bispyridiniumalkane (preferably octenidine), only a limited amount of cationic surfactant is present. More preferably, this limited amount of cationic surfactant is at most 0.5% by weight, in particular at most 0.2% by weight, such as at most 0.1% by weight or at most 0.05% by weight. In a particularly preferred embodiment, thus—in addition to component a)—no cationic surfactant is present in the preparation according to the invention.

Solvents

Moreover, the preparation optionally comprises d) solvents.

Preferred solvents are glycols and water, as well as mixtures thereof. A preferred solvent is water.

Further Active Ingredients and/or Auxiliaries

Examples of active ingredients and/or auxiliaries which may optionally be present in preparations according to the invention are skincare additives, refatting agents, perfumes, fragrances, thickeners, pH regulators and humectants. These are inter alia:

polyols, which act as skincare additives, refatting agents and humectants, such as glycerol, propylene glycol, erythritol, 1,2,6-hexanetriol, inositol, lactitol, maltitol, mannitol, methylpropanediol, phytantriol, polyglycerols, sorbitol and xylitol, with glycerol and propylene glycol being particularly preferred, glycerol esters, preferably glycerol cocoate, isopropyl myristate, isopropyl palmitate, and triglycerides, which act as refatting agents, allantoin and dexpanthenol, which can act as skincare additives, and/or pH regulators, such as sodium gluconate, lactic acid and salts thereof (such as sodium lactate), and citric acid and salts thereof.

The following constituents are preferably present in preparations according to the invention:

polyol, such as glycerol, in an amount of from 0.1 to 10% by weight, preferably 0.3 to 5% by weight, more preferably 0.5 to 1% by weight, and glycerol monoalkyl ether, such as 1-(2-ethylhexyl) glycerol ether in an amount of from 0.01 to 5% by weight, preferably 0.02 to 2% by weight, in particular 0.03 to 0.5% by weight.

According to the invention, preference is given to a preparation which comprises
i) octenidine in an amount of from 0.01 to 0.5% by weight, preferably 0.03 to 0.3% by weight, in particular 0.04 to 0.2% by weight, such as 0.05 to 0.15% by weight, for example about 0.1% by weight,
ii) amine oxide, preferably coconut fatty acid amidopropyldimethylamine oxide, as surfactant, preferably in an amount of from 0.03 to 10% by weight, more preferably 0.06 to 5% by weight, in particular 0.1 to 2.0% by weight, such as about 0.2% by weight, iii) water as solvent and
iv) allantoin, glycerol, 1-(2-ethylhexyl) glycerol ether and sodium lactate as auxiliaries.

Likewise preferred is a preparation which comprises
i) octenidine in an amount of from 0.01 to 0.5% by weight, preferably 0.03 to 0.3% by weight, in particular 0.04 to 0.2% by weight, such as 0.05 to 0.15% by weight, for example about 0.08% by weight,
ii) betaine, preferably cocamidopropylbetaine, as surfactant, preferably in an amount of from 0.03 to 10% by weight, more preferably 0.06 to 5% by weight, in particular 0.1 to 2.0% by weight, such as about 0.2% by weight,
iii) water as solvent and
iv) allantoin, glycerol, 1-(2-ethylhexyl) glycerol ether and sodium lactate as auxiliaries.

4. Presentation Forms of the Preparation

The disinfectant preparation according to the invention is non-solid, i.e. is a semi-solid or a liquid preparation.

Preferably, the preparation is liquid, where the liquid preparation is preferably an aqueous, an aqueous-alcoholic or an alcoholic solution. Typically, preparations according to the invention are thus in the form of aqueous solutions, preferably as alcohol-containing aqueous solutions. Examples of wound and mucosa antiseptics with a content of bispyridiniumalkane are disclosed in DE 10 2009 049 504 A1.

Semi-solid preparations are an alternative.

Semi-Solid Preparations

Salves (Latin unguenta) are spreadable preparations which are intended for use by application to or rubbing on the skin. They consist of one or more salve bases (such as Vaseline, wool grease, lanolin etc.), into which the active ingredient is incorporated. The active ingredient should be dissolved or finely distributed. In order to increase the solubility, salves often comprise water or oils. In a salve, however, the fat/oil fraction is higher than the water fraction.

For salves according to the invention, the viscosity is generally 500 to 15 000 mPa·s, preferably 1000 to 10 000 mPa·s, measured using a rotary viscometer at 95 s$^{-1}$ and 20° C.

The preparations according to the invention are for example in the form of aqueous-alcoholic gels (hydrogels). Hydrogels are valued on account of their transparency and the non-greasy character. Lipophilic gels (oleogels) are likewise used on account of their aesthetic appearance and their consistency-imparting properties. Gels are intended primarily for external use and should be applied thinly.

A hydrogel is a mostly translucent mass which is produced with the help of cellulose derivatives, gelatine, tragacanth, carbopol or similar swelling substances using water and glycerol. As a result of the evaporation of the water, they have a cooling effect.

Emulsion is understood as meaning preparations which are composed of immiscible liquids, e.g. oil and water. A distinction is made between W/O (water-in-oil) and O/W (oil-in-water) and ambiphilic emulsions. These have to be shaken vigorously prior to use. Adding an emulsifier makes it possible to very finely distribute the liquids within one another and as a result the emulsions are stable, i.e. the oil and the water do not separate again. Depending on the type of application, emulsions are intended for internal or external use. Emulsions for external use are often referred to as lotions. Here, an oil-in-water emulsion is present.

Preferably, the preparation is in the form of a hydrogel. Here, preference is given to an embodiment in which the preparation is formulated as a composition that is applied topically (externally).

According to the invention, the preparation can comprise further active ingredients which increase the efficacy of component a), i.e. for example octenidine, and which can be used in a considerably lower concentration than in the known commercial products if they are combined with bispyridiniumalkane. As a result, the existing disadvantages can be reduced, at times considerably. These further active ingredients include: clotrimazole and other locally active antimycotics, cortisones, tretinoin, benzoyl peroxide, aciclovir, local anaesthetics (e.g. benzocaine, lidocaine, polidocanol and the like), antibiotics, bufexamac etc.

The preparation of examples of semi-solid preparations with a content of bispyridiniumalkane is described in DE 10 2012 215 511 A1, cf. also DE 10 2005 045 145 A1.

The (semi-solid or liquid) preparation according to the invention is preferably transparent. This facilitates the observation of disinfected areas.

Example formulations I and II of preparations according to the invention are given below (data in % by weight):

|  | I<br>*//* | II<br>*//* |
|---|---|---|
| Octenidine | 0.01-0.2/<br>0.02-0.1/<br>0.05 | 0.01-0.2/<br>0.02-0.1/<br>0.05 |
| Propylene glycol | 2-20/5-15/<br>9.95 | 2-20/5-15/<br>9.95 |
| 2-Propanol | — | 2-20/5-15/<br>9.95 |
| Component b), particularly preferably erythrosine (CI45430) | 0.01-0.2/<br>0.02-0.1/<br>0.05 | 0.01-0.2/<br>0.02-0.1/<br>0.05 |
| Hydroxyethylcellulose | 0.5-10/<br>1-5/2.50 | 0.5-10/<br>1-5/2.50 |
| Demineralized water | Remainder | Remainder |

*preferably
**more preferably
***in particular about

Moreover, a preparation is preferred which comprises 0.05 to 0.15% by weight of octenidine, 25 to 35% by weight of n-propanol and 40 to 50% by weight of isopropanol.

Moreover, a preparation is preferred which comprises 0.05 to 0.15% by weight of octenidine and 60 to 70% by weight of isopropanol.

Moreover, a preparation is preferred which comprises 0.05 to 0.15% by weight of octenidine, 1.5 to 2.5% by weight of phenoxyethanol, and in each case less than 1% by weight of glycerol, sodium gluconate and coamidopropylbetaine.

Furthermore, a preparation is preferred which comprises 0.02 to 0.08% by weight of octenidine, 5 to 15% by weight of propylene glycol and 1.5 to 3.5% by weight of cellulose derivative.

5. Application

The disinfectant preparations according to the invention are used in the customary manner on animate or inanimate surfaces, in particular human skin. According to the present invention, the preparation is preferably used for the skin antisepsis of undamaged skin. Alternatively, the preparation can also be used for wound antisepsis, hand disinfection and for surface disinfection.

According to one embodiment, the preparation according to the invention is used for treating wounds. Here, an emulsifier-free formulation is preferably chosen which comprises a high degree of moisturizing factors (e.g. a gel).

Consequently, the invention also relates to a non-solid disinfectant preparation for use in a method for the disinfection of skin, wound or mucosa, in particular in people.

The method is preferably a preoperative measure and/or a measure before puncture or injection, where the operation which follows the disinfection is preferably an injection, vasopuncture or vascular catheter puncture.

Furthermore, the invention relates to the use of a dye selected from xanthene dyes, azo dyes and polyterpene compounds for colouring a non-solid disinfectant preparation which comprises one or more bispyridiniumalkanes, where the preparation is free from fluorescein and salts thereof.

The advantages of the present invention arise in particular from the following examples. Unless stated otherwise, percentages refer to the weight (% by weight).

EXAMPLES

No in-vitro method was hitherto known for being able to rapidly examine (i.e. screen) the potential impairment of the remanent effect of antiseptic active ingredients due to added dyes, and specifically in particular in the presence of large amounts of solvents, such as alcohols. Method A below has been newly developed for this screening and does not include in the evaluation of the experiment the immediate effect of any alcohols present in a product (such as ethanol, 1- and 2-propanol) and specifically tests the remanent effect of octenidine.

Method A 0.2 ml of the test preparation was spread to the edge on a tile measuring 5×5 cm and left to dry optically. Here, solvents evaporate and the antiseptic active ingredient (octenidine was tested) remains on the tile.

Then, 0.1 ml of bacteria suspension (test germ S. aureus ATCC 6538, starting germ count of the solution $10^6$ CFU/ml, on the tile then $10^5$ CFU/ml) is applied to an area of 3×3 cm on the tile. After the corresponding contact time, the tile is transferred to a container filled with glass beads (diameter 3-4 mm) and 10 ml of neutralization solution (TLSH) and shaken for 2 minutes on a horizontal shaker at 200 rpm. Finally, a germ count determination is performed by means of dilution series. The dilution stages $10^0$, $10^{-1}$, $10^{-2}$ and $10^{-3}$ are plated out. The agar plates are incubated for 24-48 hours at 36±1° C.

The CFU/ml resulting therefrom is used to calculate the logarithmic reduction factor (RF) for the preparations and the water control. A high 1 g reduction factor means good bactericidal efficacy of the preparation.

Since the addition of dye must not inhibit the efficacy of the commercially available product Octeniderm® colourless, the formulations of Octeniderm® with dyes must have the same reduction factor as the product Octeniderm® colourless.

Method B

Method B serves to investigate the colour spectrum of coloured preparations according to the invention.

For this, the samples to be tested are measured in 10 mm cuvettes on a Lico 690 instrument from Hach Lange. The L*a*b* values are obtained as the result. For the purposes of calibrating the instrument, demineralized water is measured in 10 mm cuvettes.

By reference to the three-dimensional colour diagram, the measured Lab values can be assigned to the particular samples.

Used light source and standard observer: C/2
(C: Colour temperature of 5600 kelvin,
2° standard observer→DIN 5033 Part 2: Definition of the spectral sensitivity of the three cone types of the light-adapted eye, describes the viewing of the coloured area (10°>2°))

Measurement by Means of Spectral Method:

The white light of the halogen lamp is split into its spectral fractions by means of a concave grating and the degree of transmission of the sample is measured in the wavelength range from 380 nm to 720 nm in 10 nm steps. The measured degrees of transmission are used to calculate the standard colour values X, Y and Z taking into consideration the set type of light and standard observer (see DIN 5033 Part 4). Since these do not form a rectangular coordinate system and produce no direct information about lightness or colour saturation of the sample, they are transformed to the CIE-L*a*b* system for the purposes of better illustration and graphical representation.

Example 1

The following formulations 1A to 1C were prepared (Table I: data of the fractions in % by weight).

TABLE I

|  | 1A | 1B | 1C |
|---|---|---|---|
| Erythrosine (CI 45430) | 0.05 | — | — |
| D&C Orange 4 (CI 15510) | — | 0.05 | — |
| Annatto 2% AS (CI 75120) (tradename of Pharmorgana) | — | — | 1.00 |
| 1-Propanol | 30.00 | 30.00 | 30.00 |
| 2-Propanol | 45.00 | 45.00 | 45.00 |
| Demineralized water | 24.85 | 24.85 | 23.90 |
| Octenidine | 0.10 | 0.10 | 0.10 |

The microbiological remanence effect of the formulations 1A to 1C was examined using method A. The results are shown below in Table II.

TABLE II

|  | 3 h | 6 h | 24 h |
|---|---|---|---|
| Experiment series 1 |  |  |  |
| Octeniderm | 3.9 | 3.9 | 4.0 |
| 1A | 3.9 | 3.9 | 4.0 |
| 1B | 2.3 | 3.9 | 4.0 |
| Experiment series 2 |  |  |  |
| Octeniderm | 3.2 | 3.0 | — |
| 1C | 3.2 | 3.0 | — |

It is evident from this that the formulations 1A and 1B exhibit an equally good remanence effect as octeniderm over 24 hours. The formulation 1C has a remanence effect comparable with octeniderm over 6 hours.

Example 2

The following formulations 2A and 2B were prepared (Table III, data of the fractions in % by weight).

TABLE III

|  | 2A | 2B |
|---|---|---|
| Erythrosine (CI 45430) | 0.05 | — |
| Annatto 2% AS (CI 75120) | — | 1.00 |
| 1-Propanol | 30.00 | 30.00 |
| 2-Propanol | 45.00 | 45.00 |

TABLE III-continued

|  | 2A | 2B |
|---|---|---|
| Demineralized water | 24.85 | 23.90 |
| Octenidine | 0.10 | 0.10 |

The formulations 2A and 2B were tested using method B and as regards their stability, and specifically samples were stored in each case at room temperature, 25° C. and 40° C. for 1 or 3 months. Furthermore, in order to be able to assess the skin coloration of the formulations, samples were applied to the inside of the forearm of a test person using a cotton bud (10 mm tip) and assessed visually. The results are shown below in Table IV.

TABLE IV

|  | Parameter | Zero value | 1 month | | | 3 months | | |
|---|---|---|---|---|---|---|---|---|
|  |  |  | +25° C. | +40° C. | RTL* | +25° C. | +40° C. | RTL* |
| 2A | Optics of the solution | clear, pink | clear, pink | clear, pink | clear, pink | clear, pink | clear, pink | clear, pink, slightly darker compared to the samples at +25/40° C. |
|  | Skin coloration | rosé-pink | rosé-pink | rosé-pink | rosé-pink | rosé-pink | rosé-pink | rosé-pink |
|  | L | 62.5 | 63.1 | 62.2 | 62.8 | 63.1 | 63.1 | 61.9 |
|  | A | 72.5 | 72.3 | 72.0 | 72.6 | 75 | 75.1 | 72.8 |
|  | B | 37.0 | 38.0 | 37.2 | 38.2 | 38.4 | 38.7 | 54.2 |
| 2B | Optics of the solution | clear, red-orange | clear, red-orange | clear, red-orange | clear, red-orange | clear, red-orange | clear, red-orange, somewhat paler than for the sample at +25° C. | clear, red-orange, somewhat paler than for the sample at +25° C. |
|  | Skin coloration | orange | orange | orange | orange | orange | orange | orange |
|  | L | 76.8 | 79.0 | 80.0 | 79.1 | 81.5 | 80.7 | 78.4 |
|  | A | 29.3 | 25.7 | 24.2 | 25.8 | 21.6 | 22.7 | 26.6 |
|  | B | 127.6 | 131.3 | 132.4 | 131.4 | 134.2 | 133.2 | 130.4 |

(*RTL = room temperature, light)

The results in Table IV show that the formulations 2A and 2B exhibit excellent stability, even upon prolonged storage over several months at elevated temperature, the colour shade in each case advantageously remaining virtually unchanged.

The invention claimed is:

1. A non-solid disinfectant preparation which comprises
a) octenidine dihydrochloride and
b) erythrosine, and
c) 40 to 70% by weight of isopropanol,
wherein the composition is free from fluorescein and its salts.

2. The preparation according to claim 1, wherein the octenidine dihydrochloride is 0.005 to 1.0% by weight based on the total weight of the preparation.

3. The preparation according to claim 1, further comprising a xanthene dye selected from the group consisting of eosin, D&C Red 27 and phloxine B.

4. The preparation according to claim 1, further comprising a monoazo dye selected from the group consisting of D&C Orange 4, fast yellow and D&C Red 33.

5. The preparation according to claim 1, further comprising a carotenoid selected from the group consisting of carotene dyes and xanthophyll dyes.

6. The preparation according to claim 5, wherein the carotene dye is beta-carotene or 8'-apo-betacaroten-8'-al.

7. The preparation according to claim 5, wherein the xanthophyll dye is selected from the group consisting of luteine and annatto dyes cis- or trans-bixin and cis- or trans-norbixin.

8. The preparation according to claim 1, wherein the erythrosine is 0.01 to 0.5% by weight the total weight of the preparation.

9. The preparation according to claim 1, wherein the preparation is liquid.

10. The preparation according to claim 1, wherein the preparation is a transparent preparation.

11. The preparation according to claim 1, further comprising 25 to 35% by weight of n-propanol, wherein the octenidine dihydrochloride is 0.05 to 0.15% by weight, and the isopropanol is 40 to 50% by weight, in each case based on the total weight of the preparation.

12. The preparation according to claim 1, wherein the octenidine dihydrochloride is 0.05 to 0.15% by weight, and the isopropanol is 60 to 70% by weight, in each case based on the total weight of the preparation.

13. The preparation according to claim 1, further comprising 1.5 to 2.5% by weight of phenoxyethanol and less than 1% by weight of glycerol, sodium gluconate and cocamidopropylbetaine, wherein the octenidine dihydrochloride is 0.05 to 15% by weight, in each case based on the total weight of the preparation.

14. The preparation according to claim 1, further comprising 5 to 15% by weight of propylene glycol and 1.5 to 3.5% by weight of cellulose derivative, wherein the octenidine dihydrochloride is 0.02 to 0.08% by weight, in each case based on the total weight of the preparation.

15. A method for the disinfection of skin, wound or mucosa, comprising administering to a subject in need thereof an effective amount of a non-solid disinfectant preparation according to claim 1.

16. The method according to claim 15, wherein the method is a preoperative measure, where the operation which follows the disinfection is an injection, vasopuncture or vascular catheter puncture.

17. A method of preparing a non-solid disinfectant preparation, comprising adding erythrosine for colouring to a non-solid disinfectant preparation which comprises octenidine dihydrochloride and isopropanol, wherein the isopropanol is 40 to 70% by weight of the non-solid disinfectant preparation after addition of the erythrosine, and wherein the preparation is free from fluorescein and salts thereof.

* * * * *